US006809233B2

(12) United States Patent
Frommer

(10) Patent No.: US 6,809,233 B2
(45) Date of Patent: *Oct. 26, 2004

(54) DNA SEQUENCES FOR AN AMINO ACID TRANSPORTER PLASMIDS, BACTERIA, YEASTS AND PLANTS CONTAINING A TRANSPORTER AND THEIR USE

(75) Inventor: Wolf-Bernd Frommer, Berlin (DE)

(73) Assignee: Hoechst Schering AgrEvo GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/854,774

(22) Filed: May 14, 2001

(65) Prior Publication Data

US 2003/0051271 A1 Mar. 13, 2003

Related U.S. Application Data

(62) Division of application No. 08/964,939, filed on Nov. 5, 1997, now Pat. No. 6,245,970, which is a division of application No. 08/362,512, filed as application No. PCT/EP93/01736 on Jul. 1, 1993, now Pat. No. 5,719,043.

(30) Foreign Application Priority Data

Jul. 5, 1992 (DE) .......................................... 42 22 315

(51) Int. Cl.[7] ............................ C12N 5/10; C12N 5/14; C12N 15/29; C12N 15/82; A01H 5/00
(52) U.S. Cl. ....................... 800/286; 800/278; 800/298; 536/23.1; 536/23.6; 435/252.3; 435/254.2; 435/320.1; 435/419
(58) Field of Search ................................ 800/278, 285, 800/286, 295, 298; 435/410, 419, 468, 320.1, 252.3, 254.2; 536/23.1, 23.6

(56) References Cited

U.S. PATENT DOCUMENTS 5,719,043 A 2/1998 Frommer ................... 435/69.1

FOREIGN PATENT DOCUMENTS

DE 4204103 8/1993

OTHER PUBLICATIONS

Marvier A. et al., Biochemica et Biophysica Acta, 1998; vol. 1373, pp. 321–331.*
Schwacke R. et al., The Plant Cell, 1999, vol. 11, pp. 377–391.*
Montamat F. et al., Plant Molecular Biology, 1999, vol. 41; pp. 259–268.*
Tegeder M. et al., Plant Physiology, 2000, vol. 122, pp. 319–325.*
Popova O. et al., Plant Molecular Biology, 2003, vol. 52., pp. 569–578.*

Fourgoux–Nicol A. et al., 1999, Plant Molecular Biology 40 :857–872.*
Chen L. et al., Plant Physiology, 2001, vol. 125, pp. 1813–1820.*
Neelam A. et al., Plant Physiology, Aug. 1999, vol. 120, pp. 1049–1056.*
Broun P. et al., PNAS 2001, vol. 98, No. 16, pp. 8925–8927.*
Smith C. et al.; Nature 334: 724–726, 1988.*
Li, Z.–C., et al., (1990) "Delta pH–Dependent Amino Acid Transport Into Plasma Membrane Vesicles Isolated From Sugar Beet Leaves", Plant Physiology, vol. 94, pp. 268–277.
Li, Z.–C., et al., (1991) "Delta pH–Dependent Amino Acid Transport Into Plasma Membrane Vesicles Isolated From Sugar Beet (*Beta vulgaris L.* ) Leaves", Plant Physiology, vol. 96, pp. 1338–1344.
Tanaka, J., et al.,(1985) "The Histidine Permease Gene HIPI of Saccharomyces cerevisiae", Gene, vol. 38, pp. 205–214.
EMBL Sequence Database, Acc. No. X67124 Rel. 35, Feb. 28, 1993, A. Thaliana PPP mRNA for Amino Acid Permease I.
Frommer, W.B. et al., (1993) "Expression Cloning in Yeast of a cDNA Encoding Broad Specificity Amino Acid Permease from Arabidopsis thaliana", Proceedings of the National Academy of Sciences of USA, vol. 90, pp. 5944–5948.
Kwart, M., et al., (1993) "Differential Expression of Two Related Amino Acid Transporters with Differing Substrate Specificity in Arabidopsis thaliana", The Plant Journal, vol. 4, No. 6, pp. 993–1002.
Sentenac et al. (1992) "Cloning and expression in yeast of a plant potassium ion transport system" Science vol. 256, pp. 663–665.
Ohnishi et al (1988) Jpn. J. Genet. vol. 63, pp. 343–357.
Oxender et al. (19980) Proc. Natl. Acad. Sci, USA vol. 77, pp. 1412–1416.
Stam M, et al. "The silence of genes in transgenic plants." Ann. Bot. 79: 3–12.
Koziel MG, et al. "Optimizing expression of tansgenes with an emphasis on post–transcriptional events. " Plant Mol. Biol. 32: 393–405.
Smith Cis, et al., "Antisense RNA inhibition of polygalacturonase gene expression in transgenic tomatoes." Nature 334: 724–726.
Bush, Dr, et al, "Molecular analysis of plant sugar and amino acid transporters." J. Exp. Bot. 47: 1205–1210.

* cited by examiner

*Primary Examiner*—David T. Fox
*Assistant Examiner*—Russell Kallis
(74) *Attorney, Agent, or Firm*—Frommer Lawrence & Haug LLP

(57) ABSTRACT

There are described DNA sequences, that contain the coding region of amino acid transporters whose, introduction in a plant genome modifies the transfer of metabolites in transgenic plants, plasmids, bacteria, yeasts and plants containing these DNA sequences, as well as their use.

25 Claims, 5 Drawing Sheets

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1685 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (A) ORGANISM: Arabidopsis thaliano (ix) FEATURE:
      (A) NAME/KEY: CDS
      (B) LOCATION: 57..1511
      (D) OTHER INFORMATION: /note= "amino acid transporter"

(xi) SEQUENCE DESCRIPTION: SEQ ID NO: 1:

```
CTTAAAACAT TTATTTTATC TTCTTCTTGT TCTCTCTTTC TCTTTCTCTC ATCACT              56

ATG AAG AGT TTC AAC ACA GAA GGA CAC AAC CAC TCC ACG GCG GAA TCC           104
Met Lys Ser Phe Asn Thr Glu Gly His Asn His Ser Thr Ala Glu Ser
 1               5                  10                  15

GGC GAT GCC TAC ACC GTG TCG GAC CCG ACA AAG AAC GTC GAT GAA GAT           152
Gly Asp Ala Tyr Thr Val Ser Asp Pro Thr Lys Asn Val Asp Glu Asp
                 20                  25                  30

GGT CGA GAG AAG CGT ACC GGG ACG TGG CTT ACG GCG AGT GCG CAT ATT           200
Gly Arg Glu Lys Arg Thr Gly Thr Trp Leu Thr Ala Ser Ala His Ile
             35                  40                  45

ATC ACG GCG GTG ATA GGC TCC GGA GTG TTG TCT TTA GCA TGG GCT ATA           248
Ile Thr Ala Val Ile Gly Ser Gly Val Leu Ser Leu Ala Trp Ala Ile
 50                  55                  60

GCT CAG CTT GGT TGG ATC GCA GGG ACA TCG ATC TTA CTC ATT TTC TCG           296
Ala Gln Leu Gly Trp Ile Ala Gly Thr Ser Ile Leu Leu Ile Phe Ser
 65                  70                  75                  80

TTC ATT ACT TAC TTC ACC TCC ACC ATG CTT GCC GAT TGC TAC CGT GCG           344
Phe Ile Thr Tyr Phe Thr Ser Thr Met Leu Ala Asp Cys Tyr Arg Ala
                 85                  90                  95

CCG GAT CCC GTC ACC GGA AAA CGG AAT TAC ACT TAC ATG GAC GTT GTT           392
Pro Asp Pro Val Thr Gly Lys Arg Asn Tyr Thr Tyr Met Asp Val Val
                100                 105                 110

CGA TCT TAC CTC GGT GGT AGG AAA GTG CAG CTC TGT GGA GTG GCA CAA           440
Arg Ser Tyr Leu Gly Gly Arg Lys Val Gln Leu Cys Gly Val Ala Gln
            115                 120                 125

TAT GGG AAT CTG ATT GGG GTC ACT GTT GGT TAC ACC ATC ACT GCT TCT           488
Tyr Gly Asn Leu Ile Gly Val Thr Val Gly Tyr Thr Ile Thr Ala Ser
    130                 135                 140

ATT AGT TTG GTA GCG GTA GGG AAA TCG AAC TGC TTC CAC GAT AAA GGG           536
Ile Ser Leu Val Ala Val Gly Lys Ser Asn Cys Phe His Asp Lys Gly
145                 150                 155                 160

CAC ACT GCG GAT TGT ACT ATA TCG AAT TAT CCG TAT ATG GCG GTT TTT           584
His Thr Ala Asp Cys Thr Ile Ser Asn Tyr Pro Tyr Met Ala Val Phe
                165                 170                 175

GGT ATC ATT CAA GTT ATT CTT AGC CAG ATC CCA AAT TTC CAC AAG CTC           632
Gly Ile Ile Gln Val Ile Leu Ser Gln Ile Pro Asn Phe His Lys Leu
                180                 185                 190

TCT TTT CTT TCC ATT ATG GCC GCA GTC ATG TCC TTT ACT TAT GCA ACT           680
```

-continued

```
Ser Phe Leu Ser Ile Met Ala Ala Val Met Ser Phe Thr Tyr Ala Thr
        195                 200                 205

ATT GGA ATC GGT CTA GCC ATC GCA ACC GTC GCA GGT GGG AAA GTG GGT         728
Ile Gly Ile Gly Leu Ala Ile Ala Thr Val Ala Gly Gly Lys Val Gly
210                 215                 220

AAG ACG AGT ATG ACG GGC ACA GCG GTT GGA GTA GAT GTA ACC GCA GCT         776
Lys Thr Ser Met Thr Gly Thr Ala Val Gly Val Asp Val Thr Ala Ala
225                 230                 235                 240

CAA AAG ATA TGG AGA TCG TTT CAA GCG GTT GGG GAC ATA GCG TTC GCC         824
Gln Lys Ile Trp Arg Ser Phe Gln Ala Val Gly Asp Ile Ala Phe Ala
                245                 250                 255

TAT GCT TAT GCC ACG GTT CTC ATC GAG ATT CAG GAT ACA CTA AGA TCT         872
Tyr Ala Tyr Ala Thr Val Leu Ile Glu Ile Gln Asp Thr Leu Arg Ser
            260                 265                 270

AGC CCA GCT GAG AAC AAA GCC ATG AAA AGA GCA AGT CTT GTG GGA GTA         920
Ser Pro Ala Glu Asn Lys Ala Met Lys Arg Ala Ser Leu Val Gly Val
        275                 280                 285

TCA ACC ACC ACT TTT TTC TAC ATC TTA TGT GGA TGC ATC GGC TAT GCT         968
Ser Thr Thr Thr Phe Phe Tyr Ile Leu Cys Gly Cys Ile Gly Tyr Ala
290                 295                 300

GCA TTT GGA AAC AAT GCC CCT GGA GAT TTC CTC ACA GAT TTC GGG TTT        1016
Ala Phe Gly Asn Asn Ala Pro Gly Asp Phe Leu Thr Asp Phe Gly Phe
305                 310                 315                 320

TTC GAG CCC TTT TGG CTC ATT GAC TTT GCA AAC GCT TGC ATC GCT GTC        1064
Phe Glu Pro Phe Trp Leu Ile Asp Phe Ala Asn Ala Cys Ile Ala Val
                325                 330                 335

CAC CTT ATT GGT GCC TAT CAG GTG TTC GCG CAG CCG ATA TTC CAG TTT        1112
His Leu Ile Gly Ala Tyr Gln Val Phe Ala Gln Pro Ile Phe Gln Phe
            340                 345                 350

GTT GAG AAA AAA TGC AAC AGA AAC TAT CCA GAC AAC AAG TTC ATC ACT        1160
Val Glu Lys Lys Cys Asn Arg Asn Tyr Pro Asp Asn Lys Phe Ile Thr
        355                 360                 365

TCT GAA TAT TCA GTA AAC GTA CCT TTC CTT GGA AAA TTC AAC ATT AGC        1208
Ser Glu Tyr Ser Val Asn Val Pro Phe Leu Gly Lys Phe Asn Ile Ser
370                 375                 380

CTC TTC AGA TTG GTG TGG AGG ACA GCT TAT GTG GTT ATA ACC ACT GTT        1256
Leu Phe Arg Leu Val Trp Arg Thr Ala Tyr Val Val Ile Thr Thr Val
385                 390                 395                 400

GTA GCT ATG ATA TTC CCT TTC TTC AAC GCG ATC TTA GGT CTC ATC GGA        1304
Val Ala Met Ile Phe Pro Phe Phe Asn Ala Ile Leu Gly Leu Ile Gly
                405                 410                 415

GCA GCT TCC TTC TGG CCT TTA ACG GTT TAT TTC CCT GTG GAG ATG CAC        1352
Ala Ala Ser Phe Trp Pro Leu Thr Val Tyr Phe Pro Val Glu Met His
            420                 425                 430

ATT GCA CAA ACC AAG ATT AAG AAG TAC TCT GCT AGA TGG ATT GCG CTG        1400
Ile Ala Gln Thr Lys Ile Lys Lys Tyr Ser Ala Arg Trp Ile Ala Leu
        435                 440                 445

AAA ACG ATG TGC TAT GTT TGC TTG ATC GTC TCG CTC TTA GCT GCA GCC        1448
Lys Thr Met Cys Tyr Val Cys Leu Ile Val Ser Leu Leu Ala Ala Ala
450                 455                 460

GGA TCC ATC GCA GGA CTT ATA AGT AGT GTC AAA ACC TAC AAG CCC TTC        1496
Gly Ser Ile Ala Gly Leu Ile Ser Ser Val Lys Thr Tyr Lys Pro Phe
465                 470                 475                 480

CGG ACT ATG CAT GAG TGAGTTTGAG ATCCTCAAGA GAGTCAAAAA TATATGTAGT        1551
Arg Thr Met His Glu
                485

AGTTTGGTCT TTCTGTTAAA CTATCTGGTG TCTAAATCCA ATGAGAATGC TTTATTGC         1611

AAACTTCATG AATCTCTCTG TATCTACATC TTTCAATCTA ATACATATGA GCTCTTCC         1671
```

AAAAAAAAAA AAAA                                                         1685

(2) INFORMATION FOR SEQ ID NO: 2:

(i) SEQUENCE CHARACTERISTICS:
        (A) LENGTH: 485 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Lys Ser Phe Asn Thr Glu Gly His Asn His Ser Thr Ala Glu Ser
 1               5                  10                  15

Gly Asp Ala Tyr Thr Val Ser Asp Pro Thr Lys Asn Val Asp Glu Asp
             20                  25                  30

Gly Arg Glu Lys Arg Thr Gly Thr Trp Leu Thr Ala Ser Ala His Ile
         35                  40                  45

Ile Thr Ala Val Ile Gly Ser Gly Val Leu Ser Leu Ala Trp Ala Ile
 50                  55                  60

Ala Gln Leu Gly Trp Ile Ala Gly Thr Ser Ile Leu Leu Ile Phe Ser
 65              70                  75                  80

Phe Ile Thr Tyr Phe Thr Ser Thr Met Leu Ala Asp Cys Tyr Arg Ala
                 85                  90                  95

Pro Asp Pro Val Thr Gly Lys Arg Asn Tyr Thr Tyr Met Asp Val Val
             100                 105                 110

Arg Ser Tyr Leu Gly Gly Arg Lys Val Gln Leu Cys Gly Val Ala Gln
         115                 120                 125

Tyr Gly Asn Leu Ile Gly Val Thr Val Gly Tyr Thr Ile Thr Ala Ser
130                  135                 140

Ile Ser Leu Val Ala Val Gly Lys Ser Asn Cys Phe His Asp Lys Gly
145                  150                 155                 160

His Thr Ala Asp Cys Thr Ile Ser Asn Tyr Pro Tyr Met Ala Val Phe
                 165                 170                 175

Gly Ile Ile Gln Val Ile Leu Ser Gln Ile Pro Asn Phe His Lys Leu
             180                 185                 190

Ser Phe Leu Ser Ile Met Ala Ala Val Met Ser Phe Thr Tyr Ala Thr
         195                 200                 205

Ile Gly Ile Gly Leu Ala Ile Ala Thr Val Ala Gly Gly Lys Val Gly
210                  215                 220

Lys Thr Ser Met Thr Gly Thr Ala Val Gly Val Asp Val Thr Ala Ala
225                  230                 235                 240

Gln Lys Ile Trp Arg Ser Phe Gln Ala Val Gly Asp Ile Ala Phe Ala
                 245                 250                 255

Tyr Ala Tyr Ala Thr Val Leu Ile Glu Ile Gln Asp Thr Leu Arg Ser
             260                 265                 270

Ser Pro Ala Glu Asn Lys Ala Met Lys Arg Ala Ser Leu Val Gly Val
         275                 280                 285

Ser Thr Thr Thr Phe Phe Tyr Ile Leu Cys Gly Cys Ile Gly Tyr Ala
290                  295                 300

Ala Phe Gly Asn Asn Ala Pro Gly Asp Phe Leu Thr Asp Phe Gly Phe
305                  310                 315                 320

Phe Glu Pro Phe Trp Leu Ile Asp Phe Ala Asn Ala Cys Ile Ala Val
                 325                 330                 335

His Leu Ile Gly Ala Tyr Gln Val Phe Ala Gln Pro Ile Phe Gln Phe
             340                 345                 350
```

```
Val Glu Lys Lys Cys Asn Arg Asn Tyr Pro Asp Asn Lys Phe Ile Thr
    355                 360                 365

Ser Glu Tyr Ser Val Asn Val Pro Phe Leu Gly Lys Phe Asn Ile Ser
    370                 375                 380

Leu Phe Arg Leu Val Trp Arg Thr Ala Tyr Val Ile Thr Thr Val
385                 390                 395                 400

Val Ala Met Ile Phe Pro Phe Asn Ala Ile Leu Gly Leu Ile Gly
                405                 410                 415

Ala Ala Ser Phe Trp Pro Leu Thr Val Tyr Phe Pro Val Glu Met His
            420                 425                 430

Ile Ala Gln Thr Lys Ile Lys Lys Tyr Ser Ala Arg Trp Ile Ala Leu
        435                 440                 445

Lys Thr Met Cys Tyr Val Cys Leu Ile Val Ser Leu Leu Ala Ala Ala
    450                 455                 460

Gly Ser Ile Ala Gly Leu Ile Ser Ser Val Lys Thr Tyr Lys Pro Phe
465                 470                 475                 480

Arg Thr Met His Glu
            485

(2) INFORMATION FOR SEQ ID NO: 3:

(i) SEQUENCE CHARACTERISTICS:
        (A) LENGTH: 1740 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Arabidopsis thaliana (ix) FEATURE:
         (A) NAME/KEY: CDS
         (B) LOCATION: 80..1558
         (D) OTHER INFORMATION: /product= "amino acid transporter"

(xi) SEQUENCE DESCRIPTION: SEQ ID NO: 3:

CTATTTTATA ATTCCTCTTC TTTTTGTTCA TAGCTTTGTA ATTATAGTCT TATTTCTCTT     60

TAAGGCTCAA TAAGAGGAG ATG GGT GAA ACC GCT GCC GCC AAT AAC CAC CGT    112
                    Met Gly Glu Thr Ala Ala Ala Asn Asn His Arg
                      1               5                  10

CAC CAC CAC CAT CAC GGC CAC CAG GTC TTT GAC GTG GCC AGC CAC GAT    160
His His His His His Gly His Gln Val Phe Asp Val Ala Ser His Asp
             15                  20                  25

TTC GTC CCT CCA CAA CCG GCT TTT AAA TGC TTC GAT GAT GAT GGC CGC    208
Phe Val Pro Pro Gln Pro Ala Phe Lys Cys Phe Asp Asp Asp Gly Arg
         30                  35                  40

CTC AAA AGA ACT GGG ACT GTT TGG ACC GCG AGC GCT CAT ATA ATA ACT    256
Leu Lys Arg Thr Gly Thr Val Trp Thr Ala Ser Ala His Ile Ile Thr
     45                  50                  55

GCG GTT ATC GGA TCC GGC GTT TTG TCA TTG GCG TGG GCG ATT GCA CAG    304
Ala Val Ile Gly Ser Gly Val Leu Ser Leu Ala Trp Ala Ile Ala Gln
 60                  65                  70                  75

CTC GGA TGG ATC GCT GGC CCT GCT GTG ATG CTA TTG TTC TCT CTT GTT    352
Leu Gly Trp Ile Ala Gly Pro Ala Val Met Leu Leu Phe Ser Leu Val
                 80                  85                  90

ACT CTT TAC TCC TCC ACA CTT CTT AGC GAC TGC TAC AGA ACC GGC GAT    400
Thr Leu Tyr Ser Ser Thr Leu Leu Ser Asp Cys Tyr Arg Thr Gly Asp
             95                 100                 105
```

```
                                        -continued

GCA GTG TCT GGC AAG AGA AAC TAC ACT TAC ATG GAT GCC GTT CGA TCA    448
Ala Val Ser Gly Lys Arg Asn Tyr Thr Tyr Met Asp Ala Val Arg Ser
        110                 115                 120

ATT CTC GGT GGG TTC AAG TTC AAG ATT TGT GGG TTG ATT CAA TAC TTG    496
Ile Leu Gly Gly Phe Lys Phe Lys Ile Cys Gly Leu Ile Gln Tyr Leu
            125                 130                 135

AAT CTC TTT GGT ATC GCA ATT GGA TAC ACG ATA GCA GCT TCC ATA AGC    544
Asn Leu Phe Gly Ile Ala Ile Gly Tyr Thr Ile Ala Ala Ser Ile Ser
140                 145                 150                 155

ATG ATG GCG ATC AAG AGA TCC AAC TGC TTC CAC AAG AGT GGA GGA AAA    592
Met Met Ala Ile Lys Arg Ser Asn Cys Phe His Lys Ser Gly Gly Lys
                160                 165                 170

GAC CCA TGT CAC ATG TCC AGT AAT CCT TAC ATG ATC GTA TTT GGT GTG    640
Asp Pro Cys His Met Ser Ser Asn Pro Tyr Met Ile Val Phe Gly Val
            175                 180                 185

GCA GAG ATC TTG CTC TCT CAG GTT CCT GAT TTC GAT CAG ATT TGG TGG    688
Ala Glu Ile Leu Leu Ser Gln Val Pro Asp Phe Asp Gln Ile Trp Trp
        190                 195                 200

ATC TCC ATT GTT GCA GCT GTT ATG TCC TTC ACT TAC TCT GCC ATT GGT    736
Ile Ser Ile Val Ala Ala Val Met Ser Phe Thr Tyr Ser Ala Ile Gly
    205                 210                 215

CTA GCT CTT GGA ATC GTT CAA GTT GCA GCG AAT GGA GTT TTC AAA GGA    784
Leu Ala Leu Gly Ile Val Gln Val Ala Ala Asn Gly Val Phe Lys Gly
220                 225                 230                 235

AGT CTC ACT GGA ATA AGC ATC GGA ACA GTG ACT CAA ACA CAG AAG ATA    832
Ser Leu Thr Gly Ile Ser Ile Gly Thr Val Thr Gln Thr Gln Lys Ile
                240                 245                 250

TGG AGA ACC TTC CAA GCA CTT GGA GAC ATT GCC TTT GCG TAC TCA TAC    880
Trp Arg Thr Phe Gln Ala Leu Gly Asp Ile Ala Phe Ala Tyr Ser Tyr
            255                 260                 265

TCT GTT GTC CTA ATC GAG ATT CAG GAT ACT GTA AGA TCC CCA CCG GCG    928
Ser Val Val Leu Ile Glu Ile Gln Asp Thr Val Arg Ser Pro Pro Ala
        270                 275                 280

GAA TCG AAA ACG ATG AAG AAA GCA ACA AAA ATC AGT ATT GCC GTC ACA    976
Glu Ser Lys Thr Met Lys Lys Ala Thr Lys Ile Ser Ile Ala Val Thr
    285                 290                 295

ACT ATC TTC TAC ATG CTA TGT GGC TCA ATG GGT TAT GCC GCT TTT GGA   1024
Thr Ile Phe Tyr Met Leu Cys Gly Ser Met Gly Tyr Ala Ala Phe Gly
300                 305                 310                 315

GAT GCA GCA CCG GGA AAC CTC CTC ACC GGT TTT GGA TTC TAC AAC CCG   1072
Asp Ala Ala Pro Gly Asn Leu Leu Thr Gly Phe Gly Phe Tyr Asn Pro
                320                 325                 330

TTT TGG CTC CTT GAC ATA GCT AAC GCC GCC ATT GTT GTC CAC CTC GTT   1120
Phe Trp Leu Leu Asp Ile Ala Asn Ala Ala Ile Val Val His Leu Val
            335                 340                 345

GGA GCT TAC CAA GTC TTT GCT CAG CCC ATC TTT GCC TTT ATT GAA AAA   1168
Gly Ala Tyr Gln Val Phe Ala Gln Pro Ile Phe Ala Phe Ile Glu Lys
        350                 355                 360

TCA GTC GCA GAG AGA TAT CCA GAC AAT GAC TTC CTC AGC AAG GAA TTT   1216
Ser Val Ala Glu Arg Tyr Pro Asp Asn Asp Phe Leu Ser Lys Glu Phe
    365                 370                 375

GAA ATC AGA ATC CCC GGA TTT AAG TCT CCT TAC AAA GTA AAC GTT TTC   1264
Glu Ile Arg Ile Pro Gly Phe Lys Ser Pro Tyr Lys Val Asn Val Phe
380                 385                 390                 395

AGG ATG GTT TAC AGG AGT GGC TTT GTC GTT ACA ACC ACC GTG ATA TCG   1312
Arg Met Val Tyr Arg Ser Gly Phe Val Val Thr Thr Thr Val Ile Ser
                400                 405                 410

ATG CTG ATG CCG TTT TTT AAC GAC GTG GTC GGG ATC TTA GGG GCG TTA   1360
Met Leu Met Pro Phe Phe Asn Asp Val Val Gly Ile Leu Gly Ala Leu
```

-continued

```
                 415                 420                 425
GGG TTT TGG CCC TTG ACG GTT TAT TTT CCG GTG GAG ATG TAT ATT AAG          1408
Gly Phe Trp Pro Leu Thr Val Tyr Phe Pro Val Glu Met Tyr Ile Lys
            430                 435                 440

CAG AGG AAG GTT GAG AAA TGG AGC ACG AGA TGG GTG TGT TTA CAG ATG          1456
Gln Arg Lys Val Glu Lys Trp Ser Thr Arg Trp Val Cys Leu Gln Met
        445                 450                 455

CTT AGT GTT GCT TGT CTT GTG ATC TCG GTG GTC GCC GGG GTT GGA TCA          1504
Leu Ser Val Ala Cys Leu Val Ile Ser Val Val Ala Gly Val Gly Ser
460                 465                 470                 475

ATC GCC GGA GTG ATG CTT GAT CTT AAG GTC TAT AAG CCA TTC AAG TCT          1552
Ile Ala Gly Val Met Leu Asp Leu Lys Val Tyr Lys Pro Phe Lys Ser
                480                 485                 490

ACA TAT TGATGATTAT GGACCATGAA CAACAGAGAG AGTTGGTGTG TAAAGTTTAC           1608
Thr Tyr
CATTTCAAAG AAAACTCCAA AAATGTGTAT ATTGTATGTT GTTCTCATTT CGTATGGT          1668

CATCTTTGTA ATAAAATTTA AAACTTATGT TATAAATTAT AAAAAAAAAA AAAAAAAA         1728

AAAAAAAAAA AA                                                            1740
```

(2) INFORMATION FOR SEQ ID NO: 4:

(i) SEQUENCE CHARACTERISTICS:
        (A) LENGTH: 493 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Gly Glu Thr Ala Ala Ala Asn Asn His Arg His His His His
 1               5                  10                  15

Gly His Gln Val Phe Asp Val Ala Ser His Asp Phe Val Pro Pro Gln
                20                  25                  30

Pro Ala Phe Lys Cys Phe Asp Asp Gly Arg Leu Lys Arg Thr Gly
            35                  40                  45

Thr Val Trp Thr Ala Ser Ala His Ile Ile Thr Ala Val Ile Gly Ser
 50                  55                  60

Gly Val Leu Ser Leu Ala Trp Ala Ile Ala Gln Leu Gly Trp Ile Ala
 65                  70                  75                  80

Gly Pro Ala Val Met Leu Leu Phe Ser Leu Val Thr Leu Tyr Ser Ser
                85                  90                  95

Thr Leu Leu Ser Asp Cys Tyr Arg Thr Gly Asp Ala Val Ser Gly Lys
            100                 105                 110

Arg Asn Tyr Thr Tyr Met Asp Ala Val Arg Ser Ile Leu Gly Gly Phe
        115                 120                 125

Lys Phe Lys Ile Cys Gly Leu Ile Gln Tyr Leu Asn Leu Phe Gly Ile
    130                 135                 140

Ala Ile Gly Tyr Thr Ile Ala Ala Ser Ile Ser Met Met Ala Ile Lys
145                 150                 155                 160

Arg Ser Asn Cys Phe His Lys Ser Gly Gly Lys Asp Pro Cys His Met
                165                 170                 175

Ser Ser Asn Pro Tyr Met Ile Val Phe Gly Val Ala Glu Ile Leu Leu
            180                 185                 190

Ser Gln Val Pro Asp Phe Asp Gln Ile Trp Trp Ile Ser Ile Val Ala
        195                 200                 205

Ala Val Met Ser Phe Thr Tyr Ser Ala Ile Gly Leu Ala Leu Gly Ile
    210                 215                 220
```

-continued

```
Val Gln Val Ala Ala Asn Gly Val Phe Lys Gly Ser Leu Thr Gly Ile
225                 230                 235                 240

Ser Ile Gly Thr Val Thr Gln Thr Gln Lys Ile Trp Arg Thr Phe Gln
                245                 250                 255

Ala Leu Gly Asp Ile Ala Phe Ala Tyr Ser Tyr Ser Val Val Leu Ile
                260                 265                 270

Glu Ile Gln Asp Thr Val Arg Ser Pro Pro Ala Glu Ser Lys Thr Met
            275                 280                 285

Lys Lys Ala Thr Lys Ile Ser Ile Ala Val Thr Thr Ile Phe Tyr Met
        290                 295                 300

Leu Cys Gly Ser Met Gly Tyr Ala Ala Phe Gly Asp Ala Ala Pro Gly
305                 310                 315                 320

Asn Leu Leu Thr Gly Phe Gly Phe Tyr Asn Pro Phe Trp Leu Leu Asp
                325                 330                 335

Ile Ala Asn Ala Ala Ile Val Val His Leu Val Gly Ala Tyr Gln Val
                340                 345                 350

Phe Ala Gln Pro Ile Phe Ala Phe Ile Glu Lys Ser Val Ala Glu Arg
            355                 360                 365

Tyr Pro Asp Asn Asp Phe Leu Ser Lys Glu Phe Glu Ile Arg Ile Pro
    370                 375                 380

Gly Phe Lys Ser Pro Tyr Lys Val Asn Val Phe Arg Met Val Tyr Arg
385                 390                 395                 400

Ser Gly Phe Val Val Thr Thr Thr Val Ile Ser Met Leu Met Pro Phe
                405                 410                 415

Phe Asn Asp Val Val Gly Ile Leu Gly Ala Leu Gly Phe Trp Pro Leu
                420                 425                 430

Thr Val Tyr Phe Pro Val Glu Met Tyr Ile Lys Gln Arg Lys Val Glu
            435                 440                 445

Lys Trp Ser Thr Arg Trp Val Cys Leu Gln Met Leu Ser Val Ala Cys
        450                 455                 460

Leu Val Ile Ser Val Val Ala Gly Val Gly Ser Ile Ala Gly Val Met
465                 470                 475                 480

Leu Asp Leu Lys Val Tyr Lys Pro Phe Lys Ser Thr Tyr
                485                 490
```

DNA SEQUENCES FOR AN AMINO ACID TRANSPORTER PLASMIDS, BACTERIA, YEASTS AND PLANTS CONTAINING A TRANSPORTER AND THEIR USE

This application is a divisional of application Ser. No.08/964,939 filed Nov. 5, 1997, now U.S. Pat. No. 6,245,970, which is a divisional of application Ser. No. 08/362,512 filed Jan. 5, 1995, now U.S. Pat. No. 5,719,043 granted Feb. 17, 1998 as the National Phase of PCT/EP93/01736 filed Jul. 1, 1993, designating the U.S., published as WO 94/01559, and claiming priority from German application P 4 22 2315.6 filed Jul. 5, 1992. All of the above-mentioned applications, as well as all documents cited therein and documents referenced or cited in documents cited herein, are hereby incorporated herein by reference.

BACKGROUND OF THE INVENTION

Field of the Invention

The present invention relates to DNA sequences that contain the coding region of amino acid transporters, whose introduction in a plant genome modifies the transfer of metabolites in transgenic plants, plasmids, bacteria, yeasts and plants containing these DNA sequences, as well as their use.

For many plant species it is known that the delivery of energy-rich compounds to the phloem through the cell wall takes place throughout the cell. Transporter molecules which allow the penetration of amino acids through the plant cell wall are not known.

In bacteria, numerous amino acid transport systems have been characterized. For aromatic amino acids, 5 different transporters have been described which can transport any one of phenylalanine, tyrosine and tryptophan, while the other transporters are specific for individual amino acids (see Sarsero et al., 1991, J Bacteriol 173: 3231–3234). The speed constants of the transport process indicates that the specific transport is less efficient. For several transporter proteins, the corresponding genes have been cloned. This has been achieved using transport-deficient mutants which were selected for their transport ability after transformation with DNA fragments as inserts in expression vectors (see Wallace et al., 1990, J Bacteriol 172: 3214–3220). The mutants were selected depending on their ability to grow in the presence of toxic analogues of amino acids, since the mutants cannot take these up and therefore cannot be impaired.

Corresponding complementation studies have been carried out with the eukaryotic yeast, Saccharomyces cerevisiae. Tanaka & Fink (1985, Gene 38: 205–214) describe a histidine transporter that was identified by complementation of a mutation. Vandenbol et al. (1989, Gene 83: 153–159) describe a proline transporter for Saccharomyces cerevisiae. The yeast possesses two different permeases for proline. One transports with lower efficiency and can be used also for other amino acids, and the other is proline-specific and works with high affinity. The latter was coded from the put4 gene. This carries an open reading frame for a peptide with a molecular weight of 69 kDa. The protein contains 12 membrane-penetrating regions, but does not contain any N-terminal signal sequence for secretion. This is a typical property of integral membrane proteins. The permeases process homology for arginine and for histidine permease from yeast, but not, however, for proline permease from Escherichia coli.

For plant cells, based on studies on tobacco suspension cultures, it has been found that the transport of arginine, asparagine, phenylalanine and histidine are pH and energy dependent. Since a 1,000-fold excess of leucine inhibits the transport of the other amino acids, it can be assumed, therefore, that all amino acids use the same transporter (McDaniel et al., 1982, Plant Physio 69: 246–249). Li and Bush (1991, Plant Physiol 96: 1338–1344) determined, for aliphatic, neutral amino acids, two transport systems in plasma membrane vesicles from Beta vulgaris. On the one hand, alanine, methionine, glutamine and leucine displace each other on the transporter protein. On the other hand, isoleucine, valine and threonine have mutually competitive effects. In combined competition kinetic studies (Li & Bush, 1990, Plant Physiol 94: 268–277) four different transport systems have been distinguished. Besides a transporter for all neutral amino acids, which work with low affinity, there exists a high affinity type which, however, possesses low affinity for isoleucine, threonine, valine and proline. Further transporters exist for acids as well as for basic amino acids.

The transporter molecule or gene for plant transporter proteins is not known.

SUMMARY OF THE INVENTION

There are now described DNA sequences which contain the coding region of a plant amino acid transporter, and whose information contained in the nucleotide sequence allows, by integration in a plant genome, the formation of RNA, by which a new amino acid transport activity can be introduced in the plant cells or an endogenous amino acid transporter activity can be expressed.

Under the term amino transporter is to be understood, for example a cDNA sequence that codes an amino transporter from Arabidopsis thaliana.

The identification of the coding region of the amino acid transporter is carried out by a process which allows the isolation of plant DNA sequences which code transporter molecules by means of expression in specific mutants of yeast Saccharomyces cerevisiae. For this, suitable yeast mutants have to be provided which cannot take up a substance for which the coding region of the transporter molecule has to be isolated from a plant gene library.

A mutant which cannot grow in media, with proline or citrulline as the only nitrogen source, is described by Jauniaux et al. (1987), Eur J Biochem 164: 601–606).

For the preparation of yeast strains that can be used to identify plant amino acid transporters, a yeast mutant which is not able to grow in media with proline and/or citrulline as the only nitrogen source is, for example, transformed with pFL 61 plasmid, which carries, as an insert, cDNA fragments from a cDNA library from Arabidopsis thaliana.

Further, a double mutant JT16 (Tanaka & Fink, 1985, Gene 38: 205–214) which has a deficiency in histidine synthesis (his4) and in histidine uptake (hip1) is transformed with the described pFL 61 plasmid and cultivated in a medium with addition of histidine.

It has now surprisingly been found that, in the transformation of yeast cells, certain plant cDNA fragments can complement the yeast mutation. By analysis of the properties of the proteins coded from the cDNA it can be shown that a coding region that codes a plant amino acid transporter with a wide specificity spectrum is responsible for the complementing of the mutation (see example 3).

Such a coding region of an amino acid transporter is shown, for example, by one of the following nucleotide sequences:

1. Sequence:

```
CTTAAAACAT TTATTTTATC TTCTTCTTGT TCTCTCTTTC TCTTTCTCTC ATCACT      56    (Seq. ID No. 1)

ATG AAG AGT TTC AAC ACA GAA GGA CAC AAC CAC TCC ACG GCG GAA        101
Met Lys Ser Phe Asn Thr Glu Gly His Asn His Ser Thr Ala Glu
1               5                   10                  15

TCC GGC GAT GCC TAC ACC GTG TCG GAC CCG ACA AAG AAC GTC GAT        146
Ser Gly Asp Ala Tyr Thr Val Ser Asp Pro Thr Lys Asn Val Asp
                20                  25                  30

GAA GAT GGT CGA GAG AAG CGT ACC GGG ACG TGG CTT ACG GCG AGT        191
Glu Asp Gly Arg Glu Lys Arg Thr Gly Thr Trp Leu Thr Ala Ser
                    35                  40                  45

GCG CAT ATT ATC ACG GCG GTG ATA GGC TCC GGA GTG TTG TCT TTA        236
Ala His Ile Ile Thr Ala Val Ile Gly Ser Gly Val Leu Ser Leu
                        50                  55                  60

GCA TGG GCT ATA GCT CAG CTT GGT TGG ATC GCA GGG ACA TCG ATC        281
Ala Trp Ala Ile Ala Gln Leu Gly Trp Ile Ala Gly Thr Ser Ile
                    65                  70                  75

TTA CTC ATT TTC TCG TTC ATT ACT TAC TTC ACC TCC ACC ATG CTT        326
Leu Leu Ile Phe Ser Phe Ile Thr Tyr Phe Thr Ser Thr Met Leu
                    80                  85                  90

GCC GAT TGC TAC CGT GCG CCG GAT CCC GTC ACC GGA AAA CGG AAT        371
Ala Asp Cys Tyr Arg Ala Pro Asp Pro Val Thr Gly Lys Arg Asn
                    95                  100                 105

TAC ACT TAC ATG GAC GTT GTT CGA TCT TAC CTC GGT GGT AGG AAA        416
Tyr Thr Tyr Met Asp Val Val Arg Ser Tyr Leu Gly Gly Arg Lys
                    110                 115                 120

GTG CAG CTC TGT GGA GTG GCA CAA TAT GGG AAT CTG ATT GGG GTC        461
Val Gln Leu Cys Gly Val Ala Gln Tyr Gly Asn Leu Ile Gly Val
                    125                 130                 135

ACT GTT GGT TAC ACC ATC ACT GCT TCT ATT AGT TTG GTA GCG GTA        506
Thr Val Gly Tyr Thr Ile Thr Ala Ser Ile Ser Leu Val Ala Val
                    140                 145                 150

GGG AAA TCG AAC TGC TTC CAC GAT AAA GGG CAC ACT GCG GAT TGT        551
Gly Lys Ser Asn Cys Phe His Asp Lys Gly His Thr Ala Asp Cys
                    155                 160                 165

ACT ATA TCG AAT TAT CCG TAT ATG GCG GTT TTT GGT ATC ATT CAA        596
Thr Ile Ser Asn Tyr Pro Tyr Met Ala Val Phe Gly Ile Ile Gln
                    170                 175                 180

GTT ATT CTT AGC CAG ATC CCA AAT TTC CAC AAG CTC TCT TTT CTT        641
Val Ile Leu Ser Gln Ile Pro Asn Phe His Lys Leu Ser Phe Leu
                    185                 190                 195

TCC ATT ATG GCC GCA GTC ATG TCC TTT ACT TAT GCA ACT ATT GGA        686
Ser Ile Met Ala Ala Val Met Ser Phe Thr Tyr Ala Thr Ile Gly
                    200                 205                 210

ATC GGT CTA GCC ATC GCA ACC GTC GCA GGT GGG AAA GTG GGT AAG        731
Ile Gly Leu Ala Ile Ala Thr Val Ala Gly Gly Lys Val Gly Lys
                    215                 220                 225
```

-continued

```
ACG AGT ATG ACG GGC ACA GCG GTT GGA GTA GAT GTA ACC GCA GCT      776
Thr Ser Met Thr Gly Thr Ala Val Gly Val Asp Val Thr Ala Ala
            230                 235                 240

CAA AAG ATA TGG AGA TCG TTT CAA GCG GTT GGG GAC ATA GCG TTC      821
Gln Lys Ile Trp Arg Ser Phe Gln Ala Val Gly Asp Ile Ala Phe
            245                 250                 255

GCC TAT GCT TAT GCC ACG GTT CTC ATC GAG ATT CAG GAT ACA CTA      866
Ala Tyr Ala Tyr Ala Thr Val Leu Ile Glu Ile Gln Asp Thr Leu
            260                 265                 270

AGA TCT AGC CCA GCT GAG AAC AAA GCC ATG AAA AGA GCA AGT CTT      911
Arg Ser Ser Pro Ala Glu Asn Lys Ala Met Lys Arg Ala Ser Leu
            275                 280                 285

GTG GGA GTA TCA ACC ACT TTT TTC TAC ATC TTA TGT GGA TGC          956
Val Gly Val Ser Thr Thr Thr Phe Phe Tyr Ile Leu Cys Gly Cys
            290                 295                 300

ATC GGC TAT GCT GCA TTT GGA AAC AAT GCC CCT GGA GAT TTC CTC     1001
Ile Gly Tyr Ala Ala Phe Gly Asn Asn Ala Pro Gly Asp Phe Leu
            305                 310                 315

ACA GAT TTC GGG TTT TTC GAG CCC TTT TGG CTC ATT GAC TTT GCA     1046
Thr Asp Phe Gly Phe Phe Glu Pro Phe Trp Leu Ile Asp Phe Ala
            320                 325                 330

AAC GCT TGC ATC GCT GTC CAC CTT ATT GGT GCC TAT CAG GTG TTC     1091
Asn Ala Cys Ile Ala Val His Leu Ile Gly Ala Tyr Gln Val Phe
            335                 340                 345

GCG CAG CCG ATA TTC CAG TTT GTT GAG AAA AAA TGC AAC AGA AAC     1136
Ala Gln Pro Ile Phe Gln Phe Val Glu Lys Lys Cys Asn Arg Asn
            350                 355                 360

TAT CCA GAC AAC AAG TTC ATC ACT TCT GAA TAT TCA GTA AAC GTA     1181
Tyr Pro Asp Asn Lys Phe Ile Thr Ser Glu Tyr Ser Val Asn Val
            365                 370                 375

CCT TTC CTT GGA AAA TTC AAC ATT AGC CTC TTC AGA TTG GTG TGG     1226
Pro Phe Leu Gly Lys Phe Asn Ile Ser Leu Phe Arg Leu Val Trp
            380                 385                 390

AGG ACA GCT TAT GTG GTT ATA ACC ACT GTT GTA GCT ATG ATA TTC     1271
Arg Thr Ala Tyr Val Val Ile Thr Thr Val Val Ala Met Ile Phe
            395                 400                 405

CCT TTC TTC AAC GCG ATC TTA GGT CTT ATC GGA GCA GCT TCC TTC     1316
Pro Phe Phe Asn Ala Ile Leu Gly Leu Ile Gly Ala Ala Ser Phe
            410                 415                 420

TGG CCT TTA ACG GTT TAT TTC CCT GTG GAG ATG CAC ATT GCA CAA     1361
Trp Pro Leu Thr Val Tyr Phe Pro Val Glu Met His Ile Ala Gln
            425                 430                 435

ACC AAG ATT AAG AAG TAC TCT GCT AGA TGG ATT GCG CTG AAA ACG     1406
Thr Lys Ile Lys Lys Tyr Ser Ala Arg Trp Ile Ala Leu Lys Thr
            440                 445                 450

ATG TGC TAT GTT TGC TTG ATC GTC TCG CTC TTA GCT GCA GCC GGA     1451
Met Cys Tyr Val Cys Leu Ile Val Ser Leu Leu Ala Ala Ala Gly
            455                 460                 465
```

-continued

```
TCC ATC GCA GGA CTT ATA AGT AGT GTC AAA ACC TAC AAG CCC TTC    1496
Ser Ile Ala Gly Leu Ile Ser Ser Val Lys Thr Tyr Lys Pro Phe
            470                 475                 480

CGG ACT ATG CAT GAG TGAGTTTGAG ATCCTCAAGA GAGTCAAAAA            1541
Arg Thr Met His Glu
                485

TATATGTAGT AGTTTGGTCT TTCTGTTAAA CTATCTGGTG TCTAAATCCA          1591

ATGAGAATGC TTTATTGCTA AAACTTCATG AATCTCTCTG TATCTACATC          1641

TTTCAATCTA ATACATATGA GCTCTTCCAA AAAAAAAAAA AAAA                1685

2. Sequence:
                   CTATTTTAT AATTCCTCTT CTTTTTTGTTC      29  (Seq. ID No. 3)
ATAGCTTTGT AATTATAGTC TTATTTCTCT TTAAGGCTCA ATAAGAGGAG           79

ATG GGT GAA ACC GCT GCC GCC AAT AAC CAC CGT CAC CAC CAC CAT   124
Met Gly Glu Thr Ala Ala Ala Asn Asn His Arg His His His His
1               5                   10                  15

CAC GGC CAC CAG GTC TTT GAC GTG GCC AGC CAC GAT TTC GTC CCT   169
His Gly His Gln Val Phe Asp Val Ala Ser His Asp Phe Val Pro
                20                  25                  30

CCA CAA CCG GCT TTT AAA TGC TTC GAT GAT GAT GGC CCC CTC AAA   214
Pro Gln Pro Ala Phe Lys Cys Phe Asp Asp Asp Gly Arg Leu Lys
                35                  40                  45

AGA ACT GGG ACT GTT TGG ACC GCG AGC GCT CAT ATA ATA ACT GCG   259
Arg Thr Gly Thr Val Trp Thr Ala Ser Ala His Ile Ile Thr Ala
                50                  55                  60

GTT ATC GGA TCC GGC GTT TTG TCA TTG GCG TGG GCG ATT GCA CAG   304
Val Ile Gly Ser Gly Val Leu Ser Leu Ala Trp Ala Ile Ala Gln
                65                  70                  75

CTC GGA TGG ATC GCT GGC CCT GCT GTG ATG CTA TTG TTC TCT CTT   349
Leu Gly Trp Ile Ala Gly Pro Ala Val Met Leu Leu Phe Ser Leu
                80                  85                  90

GTT ACT CTT TAC TCC TCC ACA CTT CTT AGC GAC TGC TAC AGA ACC   394
Val Thr Leu Tyr Ser Ser Thr Leu Leu Ser Asp Cys Tyr Arg Thr
                95                  100                 105

GGC GAT GCA GTG TCT GGC AAC AGA AAC TAC ACT TAC ATG GAT GCC   439
Gly Asp Ala Val Ser Gly Lys Arg Asn Tyr Thr Tyr Met Asp Ala
                110                 115                 120

GTT CGA TCA ATT CTC GGT GGG TTC AAG TTC AAG ATT TGT GGG TTG   484
Val Arg Ser Ile Leu Gly Gly Phe Lys Phe Lys Ile Cys Gly Leu
                125                 130                 135

ATT CAA TAC TTG AAT CTC TTT GGT ATC GCA ATT GGA TAC ACG ATA   529
Ile Gln Tyr Leu Asn Leu Phe Gly Ile Ala Ile Gly Tyr Thr Ile
                140                 145                 150

GCA GCT TCC ATA AGC ATG ATG GCG ATC AAG AGA TCC AAC TGC TTC   574
Ala Ala Ser Ile Ser Met Met Ala Ile Lys Arg Ser Asn Cys Phe
                155                 160                 165
```

```
CAC AAG AGT GGA GGA AAA GAC CCA TGT CAC ATG TCC AGT AAT CCT  619
His Lys Ser Gly Gly Lys Asp Pro Cys His Met Ser Ser Asn Pro
                170                 175                 180

TAC ATG ATC GTA TTT GGT GTG GCA GAG ATC TTG CTC TCT CAG GTT  664
Tyr Met Ile Val Phe Gly Val Ala Glu Ile Leu Leu Ser Gln Val
                185                 190                 195

CCT GAT TTC GAT CAG ATT TGG TGG ATC TCC ATT GTT GCA GCT GTT  709
Pro Asp Phe Asp Gln Ile Trp Trp Ile Ser Ile Val Ala Ala Val
                200                 205                 210

ATG TCC TTC ACT TAC TCT GCC ATT GGT CTA GCT CTT GGA ATC GTT  754
Met Ser Phe Thr Tyr Ser Ala Ile Gly Leu Ala Leu Gly Ile Val
                215                 220                 225

CAA GTT GCA GCG AAT GGA GTT TTC AAA GGA AGT CTC ACT GGA ATA  799
Gln Val Ala Ala Asn Gly Val Phe Lys Gly Ser Leu Thr Gly Ile
                230                 235                 240

AGC ATC GGA ACA GTG ACT CAA ACA CAG AAG ATA TGG AGA ACC TTC  844
Ser Ile Gly Thr Val Thr Gln Thr Gln Lys Ile Trp Arg Thr Phe
                245                 250                 255

CAA GCA CTT GGA GAC ATT GCC TTT GCG TAC TCA TAC TCT GTT GTC  889
Gln Ala Leu Gly Asp Ile Ala Phe Ala Tyr Ser Tyr Ser Val Val
                260                 265                 270

CTA ATC GAG ATT CAG GAT ACT GTA AGA TCC CCA CCG GCG GAA TCG  934
Leu Ile Glu Ile Gln Asp Thr Val Arg Ser Pro Pro Ala Glu Ser
                275                 280                 285

AAA ACG ATG AAG AAA GCA ACA AAA ATC AGT ATT GCC GTC ACA ACT  979
Lys Thr Met Lys Lys Ala Thr Lys Ile Ser Ile Ala Val Thr Thr
                290                 295                 300

ATC TTC TAC ATG CTA TGT GGC TCA ATG GGT TAT GCC GCT TTT GGA  1024
Ile Phe Tyr Met Leu Cys Gly Ser Met Gly Tyr Ala Ala Phe Gly
                305                 310                 315

GAT GCA GCA CCG GGA AAC CTC CTC ACC GGT TTT GGA TTC TAC AAC  1069
Asp Ala Ala Pro Gly Asn Leu Leu Thr Gly Phe Gly Phe Tyr Asn
                320                 325                 330

CCG TTT TGG CTC CTT GAC ATA GCT AAC GCC GCC ATT GTT GTC CAC  1114
Pro Phe Trp Leu Leu Asp Ile Ala Asn Ala Ala Ile Val Val His
                335                 340                 345

CTC GTT GGA GCT TAC CAA GTC TTT GCT CAG 000 ATC TTT GCC TTT  1159
Leu Val Gly Ala Tyr Gln Val Phe Ala Gln Pro Ile Phe Ala Phe
                350                 355                 360

ATT GAA AAA TCA GTC GCA GAG AGA TAT CCA GAC AAT GAC TTC CTC  1204
Ile Glu Lys Ser Val Ala Glu Arg Tyr Pro Asp Asn Asp Phe Leu
                365                 370                 375

AGC AAG GAA TTT GAA ATC AGA ATC CCC GGA TTT AAG TCT CCT TAC  1249
Ser Lys Glu Phe Glu Ile Arg Ile Pro Gly Phe Lys Ser Pro Tyr
                380                 385                 390

AAA GTA AAC GTT TTC AGG ATG GTT TAC AGG AGT GGC TTT GTC GTT  1294
Lys Val Asn Val Phe Arg Met Val Tyr Arg Ser Gly Phe Val Val
                395                 400                 405
```

```
ACA ACC ACC GTG ATA TCG ATG CTG ATG CCG TTT TTT AAC GAC GTG    1339
Thr Thr Thr Val Ile Ser Met Leu Met Pro Phe Phe Asn Asp Val
            410                 415                 420

GTC GGG ATC TTA GGG GCG TTA GGG TTT TGG CCC TTG ACG GTT TAT    1384
Val Gly Ile Leu Gly Ala Leu Gly Phe Trp Pro Leu Thr Val Tyr
            425                 430                 435

TTT CCG GTG GAG ATG TAT ATT AAG CAG AGG AAG GTT GAG AAA TGG    1429
Phe Pro Val Glu Met Tyr Ile Lys Gln Arg Lys Val Glu Lys Trp
            440                 445                 450

AGC ACG AGA TGG GTG TGT TTA CAG ATG CTT AGT GTT GCT TGT CTT    1474
Ser Thr Arg Trp Val Cys Leu Gln Met Leu Ser Val Ala Cys Leu
            455                 460                 465

GTG ATC TCG GTG GTC GCC GGG GTT GGA TCA ATC GCC GGA GTG ATG    1519
Val Ile Ser Val Val Ala Gly Val Gly Ser Ile Ala Gly Val Met
            470                 475                 480

CTT GAT CTT AAG GTC TAT AAG CCA TTC AAG TCT ACA TAT            1558
Leu Asp Leu Lys Val Tyr Lys Pro Phe Lys Ser Thr Tyr
            485                 490

TGATGATTAT GGACCATGAA CAACAGAGAG AGTTGGTGTG TAAAGTTTAC          1608

CATTTCAAAG AAAACTCCAA AAATGTGTAT ATTGTATGTT GTTCTCATTT          1658

CGTATGGTCT CATCTTTGTA ATAAAATTTA AAACTTATGT TATAAATTAT          1708

AAAAAAAAAA AAAAAAAAAA AAAAAAAAAA AA                            1740
```

The DNA sequences of the invention identified with the help of the transformed yeast strains, e.g., sequences SEQ ID NO:1 and 3 can be introduced into plasmids and thereby be combined with steering elements for expression in eukaryotic cells (see Example 4). These steering elements are, on the one hand, transcription promoters, and, on the other hand, transcription terminators. Plasmids can be used to transform eukaryotic cells with the aim of expression of a translatable mRNA which makes possible the synthesis of an amino acid transporter in the cells or with the aim of expression of a non-translatable RNA, which prevents synthesis of an endogenous amino acid transporter in the cells. The expression of an RNA corresponding to the inventive sequences of plant amino acid transporters modifies the plant acid metabolism, as well as total nitrogen metabolism. The economic significance of this modification is obvious. Nitrogen is the nutrient mainly responsible for limiting growth. The viability of germ lines as well as germination capacity of seeds is directly dependent on the nitrogen content of storage tissue. The formation of high value food materials with a high protein content is dependent on a sufficient nitrogen supply. Nitrogen is transported essentially in the form of amino acids. An improvement in the delivery of amino acids to their harvested parts can therefore lead to an increase in yield of agricultural plants. The individual organs allows the qualitative improvement of such organs, which, because of the demands of the utilization process, contain little nitrogen. An example is potatoes, which are grown for the production of starch. Besides this, it is possible to modify the whole plant, by which the growth of individual tissues, for example, leaves, is slowed down, while the growth of the harvested parts is increased. For this, one can imagine a lengthening of the vegetative phase of crops, which leads to an increased formation of storage substances.

Processes for the genetic modification of dicotyledonous and monocotyledonous plants are already known (see for example Gasser, C. S., Fraley, R. T., 1989, Science 244: 1293–1299; Potrykus, 191, Ann Rev Plant Mol Biol Plant Physiol 42: 205–225). For expression in plants the coding sequences must be coupled with the transcriptional regulatory elements. Such elements, called promoters, are known (EP 375091).

Further, the coding regions must be provided with transcription termination signals with which they can be correctly transcribed. Such elements are also described (see Gielen et al., 1989, EMBO J 8: 23–29). The transcriptional start region can be either native and/or homologous or foreign and/or heterologous to the host plant. If desired, termination regions are interchangeable with one another. The DNA sequence of the transcription starting and termination regions can be prepared synthetically, obtained naturally, or can be a mixture of synthetic and natural DNA constituents. For introduction of foreign genes in higher plants, a large number of cloning vectors are available that include a replication signal for E. coli and a marker which allows for the selection of the transformed cells. Examples of such vectors are pBR 322, pUC-Series, M13 mp-Series, pACYC 184, etc. Depending on the method of introduction of the desired gene in the plants, other DNA sequences may be suitable. Should the Ti- or Ri-plasmid be used, e.g., for the transformation of the plant cell, then at least the right boundary, often, however, both the right and left boundary of the Ti- and Ri-Plasmid T-DNA, is attached, as a flanking region, to the gene being introduced. The use of T-DNA for the transformation of plant cells has been intensively researched and is well described in EP 120 516; Hoekama, In: The Binary Plant Vector System, Offset-drukkerij Kanters B. V. Alblasserdam (1985), Chapter V; Fraley, et al., Crit. Rev. Plant Sci., 4:1–46 and An et al. (1985) EMBO J. 4: 277–287. Once the introduced DNA is integrate in the genome, it is generally stable there and remains in the offspring of the original transformed cells. It normally contains a selection marker which induces resistance in the transformed plant cells against a biocide or antibiotic such as kanamycin, G 418, bleomycin, hygromycin or phosphinotricin, etc. The individual marker employed should therefore allow the selection of transformed cells from cells which lack the introduced DNA.

For the introduction of DNA into a plant host cell, besides transformation using *Agrobacteria*, there are many other techniques available. These techniques include the fusion of protoplasts, microinjection of DNA and electroporation, as well as ballistic methods and virus infection. From the transformed plant material, whole plants can be regenerated in a suitable medium which contains antibiotics or biocides for selection. The resulting plants can then be tested for the presence of introduced DNA. No special demands are placed on the plasmids in injection and electroporation. Simple plasmids, such as, e.g., pUC-derivatives, can be used. Should whole plants be regenerated from such transformed cells, the presence of a selectable marker gene is necessary. The transformed cells grow within the plants in the usual manner (see also McCormick et al. (1986) Plant Cell Reports 5: 81–84). These plants can be grown normally and crossed with plants that possess the same transformed genes or different genes. The resulting hybrid individuals have the corresponding phenotypical properties.

The DNA sequences of the invention can also be introduced in plasmids and thereby combined with steering elements for an expression in prokaryotic cells. The formation of a translatable RNA sequence of a eukaryotic amino acid transporter from bacteria, in spite of the considerable differences in the membrane structures of prokaryotes and eukaryotes, means that prokaryotes can now use a eukaryotic amino acid transporter with specificity for certain substrates. This makes possible the production of bacterial strains which could be used for studies of the properties of the transporter as well as its substrate.

The invention also relates to bacteria that contain the plasmids of the invention.

The DNA sequences of the invention can also be introduced in plasmids which allow mutagenesis or a sequence modification through recombination of DNA sequences in prokaryotic or eukaryotic systems. In this way, the specificity of the amino acid transporter can be modified. Thus, the specificity of the transporter can be changed.

The invention also relates to derivatives or parts of plasmids that contain the DNA sequences of the invention and which can be used for the transformation of prokaryotic and eukaryotic cells.

By using standard processes (see Sambrook et al., 1989, Molecular Cloning: A Laboratory Manual, 2d ed., Cold Spring Harbor Laboratory Press, N.Y., USA), base exchanges can be carried out or natural or synthetic sequences can be added. For binding DNA fragments with one another, adaptors or linkers can be introduced on the fragments. Further, manipulations can be carried which prepare suitable restriction cleavage sites or remove the excess DNA or restriction cleavage sites. Where insertions, deletions or substitutions such as, for example, transitions and transversions are desired, in vitro mutagenesis, primer repair, restrictions or ligations can be used. For methods of analysis, in general, a sequence analysis, restriction analysis and other biochemical molecular biological methods can be used. After each manipulation, the DNA sequence used can be cleaved and bound with another DNA sequence. Each plasmid sequence can be cloned in the same or different plasmids.

Derivatives or parts of the DNA sequences and plasmids of the invention can also be used for the transformation of prokaryotic and eukaryotic cells. Further, the DNA sequences of the invention can be used according to standard processes for the isolation of similar sequences on the genome of plants of various species, which also code for amino acid or other oligosaccharide transporter molecules. With these sequence constructs, for the transformation of plant cells, can be prepared which modify the transport process in transgenic plants.

In order to specify related DNA sequences, gene libraries must first be prepared which are representative of the content of genes of a plant type or for the expression of genes in a plant type. The former are genomic libraries, while the latter are cDNA libraries. From these, related sequences can be isolated using the DNA sequences of the invention as probes. Once the related gene has been identified and isolated, a determination of the sequence and an analysis of the properties of the proteins coded from this sequence is possible.

In order to understand the examples forming the basis of this invention all the processes necessary for these tests and which are known per se will first of all be listed:

1. Cloning Process

For cloning in *E. coli*, the vector pBluescriptSK (Short et al., 1988, Nucl Acids Res 16: 7583–7600) was used.

For the transformation of yeasts, the vector pFL61 (Minet & Lacroute, 1990, Curr Genet 18: 287–291) was used.

For the plant transformation the gene constructs in the binary vector pBIN-Hyg were cloned.

2. Bacterial and Yeast Strains

For the pBluescriptSK vector as well as for PBinAR constructs, the *E. coli* strain XL1blue (Bullock et al., 1987, Biotechniques, 5, 376–378) was used.

As a starting strain for the expression of the cDNA library in yeast, the yeast strain 22574d (Jauniaux et al., 1987 Eur J Biochem 164: 601–606) was used.

The transformation of the plasmids in potato plants was carried out using *Agrobacterium tumefaciens* strain LBA4404 (Bevan (1984) Nucl. Acids Res 12: 8711–8720).

3. Transformation of *Agrobacterium Tumefaciens*

The transfer of the DNA in *Agrobacteria* was carried out by direct transformation by the method of Höfgen & Willmitzer (1988, Nucleic Acids Res 16: 9877). The plasmid DNA of the transformed *Agrobacterium* was isolated in accordance with the method of Birnboim and Doly (1979) (Nucl Acids Res 7: 1513–1523) and was analyzed by gel electrophoresis after suitable restriction cleavage.

4. Plant Transformation

Ten small leaves, wounded with a scalpel, of a sterile potato culture were placed in 10 ml of MS medium with 2% amino acid containing 30–50 µl of an *Agrobacterium tumefaciens* overnight culture grown under selection. After 3–5 minutes of gentle shaking, the leaves were laid out on MS medium of 1.6% glucose, 2 mg/l of zeatin ribose, 0.02 mg/l of naphthylacetic acid, 0.02 mg/l of gibberellic acid, 500 mg/l of claforan, 50 mg/l of kanamycin and 0.8% bacto agar. After incubation for one week at 25° C. and 3000 lux, the claforan concentration in the medium was reduced by half.

Deposits

The following plasmids and yeast strains were deposited at the Deutschen Sammlung von Mikroorganismen (DSM) in Braunschweig, Germany on 12.06.1992 (deposit number):

| Plasmid | pPPP1-20 | (DSM 7129) |
| Plasmid | pBinPPP1-20 | (DSM 7130) |

Other features and advantages of the present invention will become apparent from the following description of the invention which refers to the accompanying drawings.

no=time period of the uptake without competitor;

proline=time period with fourfold excess of unlabeled proline;

citrulline=time period with fourfold excess of unlabeled citrulline;

GABA=time period with fourfold excess of gamma-aminobutyric acid;

time=time in seconds;

cpm=decays counted per minute.

Figure 3:
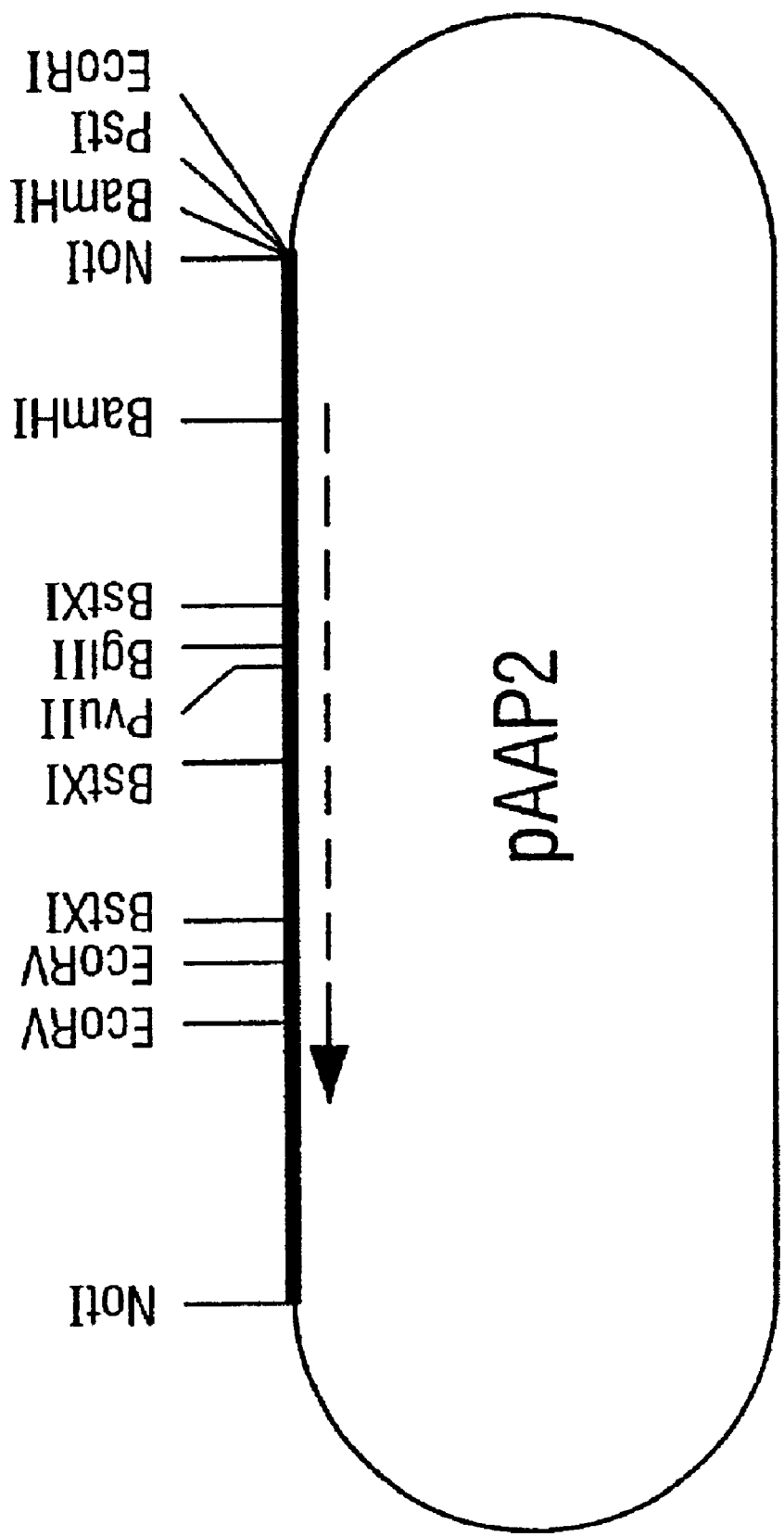

FIG. 3 shows the plasmid pAAP2 which contains the sequence SEQ NO:3 The finely drawn line corresponds to the sequence from pBluescriptSK. The thicker line represents the cDNA insert. The cleavage positions of the inserts are shown.

Figure 4:
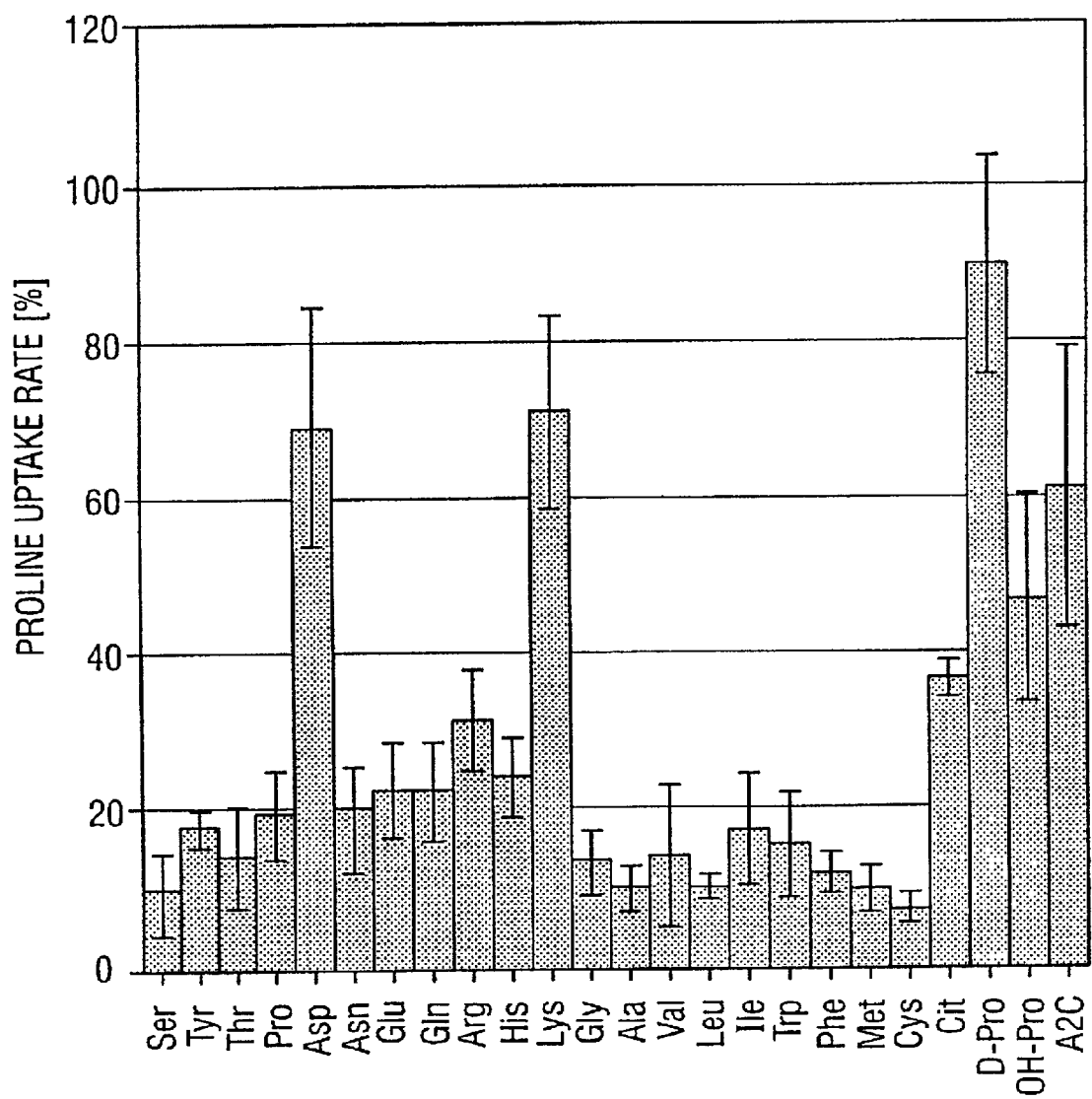

FIG. 4 shows a competition experiment with the yeast line 22574d::AAP2. In this experiment, the uptake of $^{14}$C-labeled L-proline from the medium in the presence of a fourfold excess of other amino acids or their analogues is measured. Besides the standard abbreviations for amino acids in the three letter code, the following are also used:

Cit=citrulline;

D-Pro=D-proline;

OH-Pro=hydroxyproline; and

AC2=azetidine-2-carboxylic acid.

Figure 5:
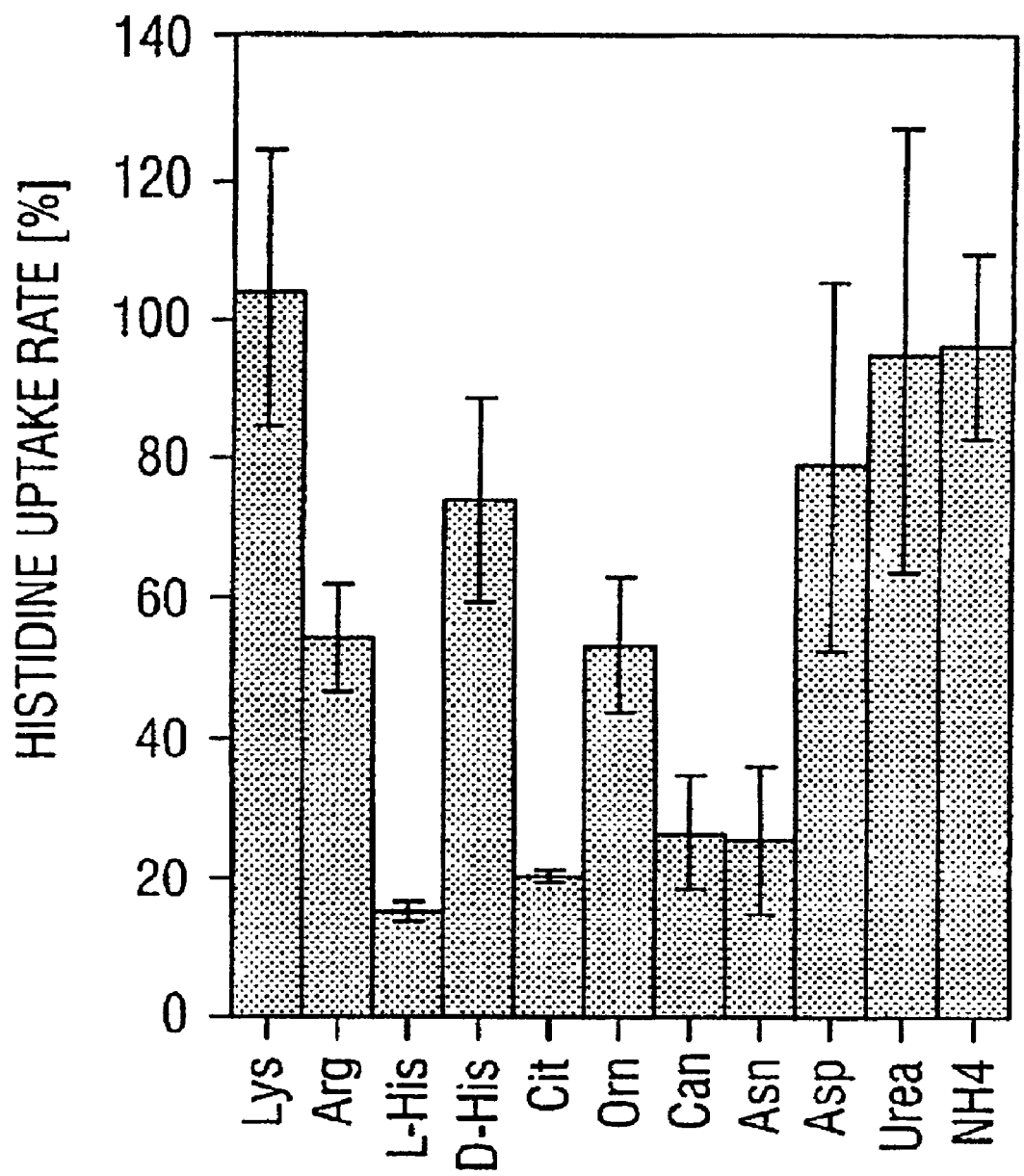

FIG. 5 shows a competition experiment with the yeast line JT16::AAP2. In this experiment, the uptake of $^{14}$C labeled L-histidine from the medium in the presence of a tenfold excess of other amino acids or their analogues is measured.

Besides the standard abbreviations for amino acids in the three letter code, the following are also used:

Cit=citrulline;

Orn=ornithine;

Can=canavanine; and

NH4=ammonium.

DETAILED DESCRIPTION OF THE PREFERRED EMBODIMENTS

The following examples describe the cloning and identification, as well as the function and use of a plant amino acid transporter.

EXAMPLE 1

Cloning of the cDNA of a Plant Amino Acid Transporter

For complementation of the proline transport mutation of the yeast strain 22574d (Jauniaux et al., 1987, Eur J Biochem 164: 601–606) and/or the histidine synthesis and transport mutation of the strain JT16 (Tanaka & Fink 1985, Gene 38: 205–214), a cDNA of young germ lines from *Arabidopsis thaliana* (two leaf stage) in the yeast expression vector pFL61 (Minet & Lacroute), 1990 Curr Genet 18: 287–291) which had been made available by Minet (Minet et al., 1992, Plant J 2: 417–422) was used. Around 1 µg of the vector with the cDNA-insert was transformed in the yeast strain 22574d and/or JT16 by the method of Dohmen et al. (1991, Yeast 7: 691–692). Yeast transformands, which could grow in media with 4 mM proline as the sole nitrogen source or in media with 6 mM histidine, were propagated. From the lines plasmid-DNA was prepared by standard methods. Clones that could complement the particular mutation contained plasmids with similar restriction type of the cDNA insert. These varied in size between 1.6 and 1.7 kb.

EXAMPLE 2

Sequence Analysis of the cDNA Insert of the Plasmid pFL61-ppp1-20

Figure 1:
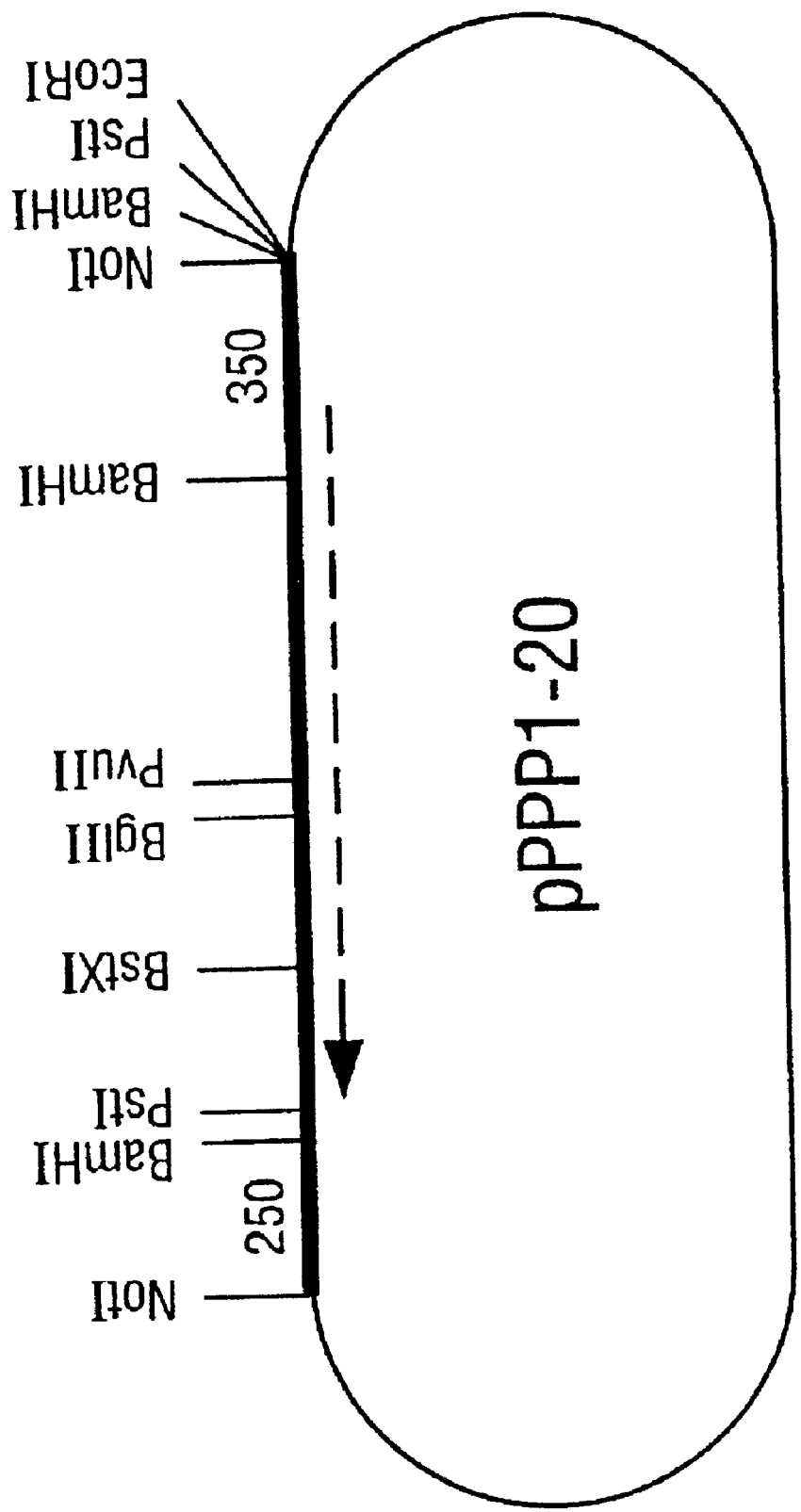
FIG. 1 shows the plasmid pPPP1-20 which contains the sequence Seq-ID No. 1. The finely drawn line corresponds to the sequence from pBluescriptSK. The thicker line represents the cDNA insert. The cleavage positions of the inserts are shown.

From a yeast line PPP1-20, obtained in a similar manner to example 1, which, in spite of the 22574d mutation, could grow with proline as the only nitrogen source, the plasmid pFL61-ppp1-20 was isolated. Its cDNA insert was prepared as a NotI fragment and cloned in the vector pBluescriptSK. In this way, the plasmid pPPP1-20 was obtained (see FIG. 1). Using synthetic oligonucleotides, the insert was sequenced by the method of Sanger et al. (1977, Proc Natl Acad Sci USA 74:5463–5467). The sequence is given above (SEQ ID No. 1).

In a similar way, from a yeast line that, in spite of the his4/hip1 double mutation, could be grown in a medium with histidine addition, the plasmid pFL61-aap2 was isolated whose insert was also cloned as a NotI fragment in pBluescriptSK. The resulting plasmid pAAP2 was sequenced and the sequence is given in SEQ ID NO:3. The plasmid pAAP2 has a similar structure to pPPP1-20 (see FIG. 1), but instead of the insert SEQ ID NO:1 carries the insert SEQ ID NO:3 (see FIG. 3).

EXAMPLE 3

Uptake Studies with $^{14}$C-labeled Protein into the Yeast Line PPP1-20 and AAP2

Figure 2:
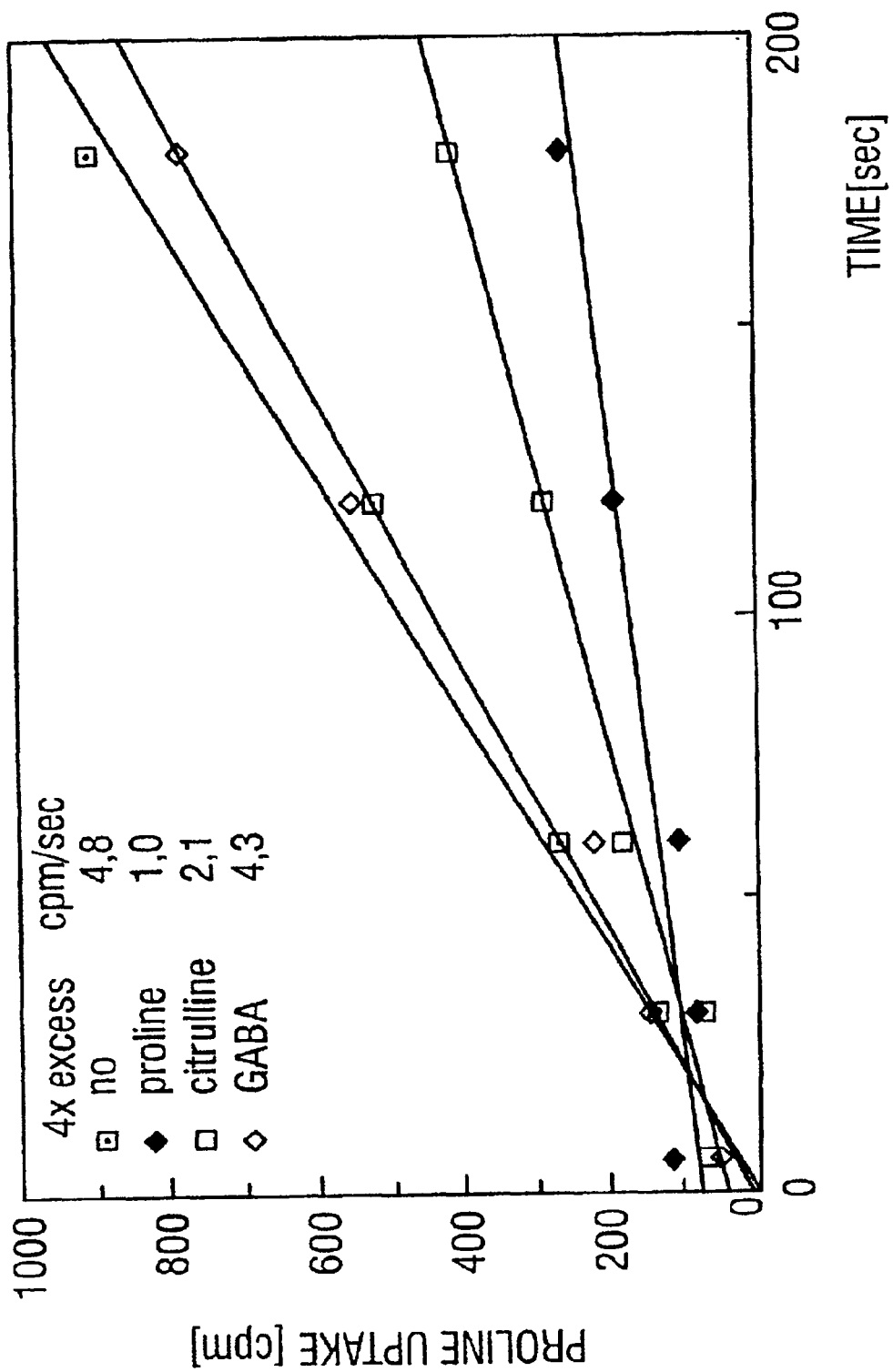
FIG. 2 shows the uptake of $^{14}$C-proline from the medium.

The yeast lines 22574d::PPP1-20 and 22574d::AAP2 that were obtained in a similar manner to Example 1 were grown in liquid medium until the culture reached the logarithmic phase. After centrifuging the culture, the cells are washed and taken up in 100 mm tris/HCl pH 4.5, 2 mM MgCl$_2$ and 0.6M sorbitol. Around 100 µL of the suspension was added to a solution of 0.5 mM L-proline plus 1 µCi $^{14}$C labeled L-proline in 100 µL of the same buffer. The uptake of the labeled amino acid was measured by the process described by Cirillo (1989, Meth Enzymol 174: 617–622). The uptake of the labeled amino acid was compared, on the one hand, in co-incubation with protein modifying substance diethyl pyrocarbonate which is an inhibitor of the amino acid transport in membrane vesicles from *Beta vulgaris*, and, on the other hand, in co-incubation with other protein modifying substances. The calculated reduction is shown in Tables I and/or III. A competition experiment in which the specificity of the transporter could be read off with various amino acids and analogues is shown in Table II for PPP1-20 and in FIG. 4 for AAP2. An analogous experiment in which a competition for histidine uptake in the line JT16::AAP2 was tested is described in Example 5. The time period for PPP1-20 is shown in FIG. 2.

EXAMPLE 4
Transformation of Plants with a Construct for Overexpression of the Coding Region of Amino Acid Transporters From the plasmid pPPP1-20 that contains the cDNA for the amino acid transporter from Arabidopsis, an internal fragment of the insert was isolated after BamHI cleavage and cloned in the BamHI cleavage position from pAJ that was first linearized with the enzyme BamHI. Then the cDNA was prepared as the EcoRI/HindIII fragment from pA7 and cloned in the vector PBIN-HYG. After transformation by *Agrobacteria*, this was inserted for infection of leaf segments of tobacco and potato.

Ten independently obtained transformands in which the presence of the intact non-rearranged chimeric gene was demonstrated using Southern blot analysis were tested for modifications of amino acid and nitrogen content. Besides this, amino acid synthesis, photosynthesis rate and transportation were tested.

EXAMPLE 5
Studies in the Uptake of $^{14}$C-labeled Histidine in the Yeast Line AAP2

The yeast line JT16::AAP2, obtained in a similar manner to Example 1, was grown in liquid medium until the culture reached the logarithmic phase. After centrifuging the culture, the cells were washed and taken up in 10 mm tris/HCl pH 4.5, 2 mm MgCl$_2$ and 0.6M sorbitol. Around 100 ml of the suspension was added to a solution of 0.5 mm L-histidine plus 1 μCi $^{14}$C-labeled L-histidine in 100 μL of the same buffer. The uptake of the labeled amino acid was measured according to the method described by von Cirillo (1989, Meth Enzymol 174: 617–622). The uptake of the labeled amino acid was compared in a competition experiment with that from different amino acids and analogues in tenfold excess. The relationships are shown in FIG. 5.

TABLE I

Inhibition of the amino acid transport in 22574d::PPP1-20 - yeast strains by protein modifying substances

| | % of transport without inhibitor |
|---|---|
| 0.1 mM DEPC (diethyl pyrocarbonate) | 65 |
| 10 μM CCCP (Carbonyl cyanide m-chlorophenylhydrazone) | <3 |
| 10 μM 2, 4 DNP (Dinitrophenol) | <3 |
| 1 mM sodium arsenate | 35 |
| 10 μM antimycin A | 29 |
| 500 μM PCMBS (p-chloromercuribenzenesulfonic acid) | 78 |

TABLE II

Competition by one, fourfold and tenfold excess of amino acids and analogues in 22574d::PPP1-20 - yeast strain

| Excess % remaining transport activity: | 1 x | 4 x | 10 x |
|---|---|---|---|
| glutamic acid | 64 | 27 | 30 |
| aspartic acid | 78 | | 27 |
| lysine | 86 | | 83 |
| histidine | 81 | 79 | 58 |
| arginine | 85 | 88 | 74 |
| threonine | — | 50 | — |
| L-proline | 49 | 21 | 14 |
| D-proline | 98 | | 95 |
| 3,4-di-OH proline | 86 | | 49 |
| azetidine-2-carboxylic acid | 91 | | 48 |
| OH-proline | 81 | | 45 |
| valine | — | 77 | 47 |
| isoleucine | — | 67 | — |
| asparagine | 64 | | 57 |
| glutamine | — | 27 | — |
| serine | 53 | | 18 |
| cysteine | — | 21 | — |
| methionine | 28 | | 8 |
| glycine | 69 | | 16 |
| alanine | 55 | 29 | 23 |
| leucine | — | | — |
| tyrosine | — | | — |
| tryptophan | 82 | 71 | 48 |
| phenylalanine | 45 | | 16 |
| citrulline | | 44 | |
| gamma-aminobutyric acid | | 90 | |

TABLE III

Inhibition of the amino acid transports in JT16::AAP2 - yeast strain by protein modifying substances

| | % of transport without inhibitor |
|---|---|
| 1 mM DEPC (Diethyl pyrocarbonate) | 3.1 ± 1.6 |
| 10 μM CCCP (Carbonyl cyanide m-chlorophenylhydrazone) | 15.6 ± 2.1 |
| 10 μM 2,4 DNP (Dinitrophenol) | 7.6 ± 1.6 |

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. An isolated DNA molecule encoding a protein with the function of a plant amino acid transporter, selected from the group consisting of:
   (a) a DNA molecule encoding a protein comprising the amino acid sequence of SEQ ID NO:2 or SEQ ID NO:4;
   (b) a DNA molecule comprising the nucleotide sequence of SEQ ID NO:1 or SEQ ID NO:3; and
   (c) a DNA molecule whose nucleotide sequence deviates from the sequence of the DNA molecule mentioned under (a) or (b) owing to the degeneracy of the genetic code.

2. A plasmid comprising the isolated DNA molecule of claim 1.

3. A method for producing a transformed host cell comprising transforming the cell to comprise the isolated DNA molecule of claim 1.

4. A transgenic plant transformed to contain the isolated DNA molecule of claim 1 and comprising an altered amount of amino acid transporter activity relative to a non-transformed plant.

5. A transgenic plant comprising a cell, wherein the cell comprises the isolated DNA molecule of claim 1.

6. A bacterium comprising the isolated DNA molecule of claim 1.

7. A bacterium comprising the plasmid of claim 2.

8. The plasmid of claim 2 further comprising a promoter operably linked to the isolated DNA molecule.

9. The plasmid of claim 2 further comprising a transcriptional termination sequence operably linked to the isolated DNA molecule.

10. The plasmid of claim 8 further comprising a transcriptional termination sequence operably linked to the isolated DNA molecule.

11. The plasmid of claim 2 wherein the isolated DNA molecule is in the sense orientation.

12. The plasmid of claim 2 wherein the isolated DNA molecule is in the anti-sense orientation.

13. A method for producing a host cell capable of an increased amount of an amino acid transporter relative to a non-transformed cell comprising transforming the cell with the plasmid of claim 11.

14. A method for producing a host cell capable of a decreased amount of an amino acid transporter relative to a non-transformed cell comprising transforming the cell with the plasmid of claim 12.

15. A yeast strain comprising the isolated DNA molecule of claim 1.

16. A method for altering the transport of metabolites in a host cell comprising transforming the cell so as to comprise the isolated DNA molecule of claim 1.

17. A cell obtainable from the method of claim 3.

18. A cell obtainable from the method of claim 13.

19. A cell obtainable from the method of claim 14.

20. A cell obtainable from the method of claim 16.

21. A transgenic plant comprising an altered amount of amino acid transporter activity by comprising a number of copies of the isolated DNA molecule of claim 1.

22. A method for producing a plant comprising:

(a) transforming plant cells to comprise the isolated DNA molecule of claim 1; and (b) regenerating a transformed plant from the plant cells.

23. The method of claim 22, wherein the isolated DNA molecule is in the anti-sense orientation and the transformed plant has a decreased amount of amino acid transporter relative to a non-transformed plant.

24. The method of claim 22, wherein the isolated DNA molecule is in the sense orientation and the transformed plant has an increased amount of amino acid transporter relative to a non-transformed plant.

25. A plant obtainable from the method of claim 22.

* * * * *